United States Patent
Pacheco Dos Santos Dias

(10) Patent No.: US 12,290,512 B2
(45) Date of Patent: May 6, 2025

(54) GEL COMPOSITION WITH AN ANAESTHETIC EFFECT OF SHORT AND LONG TERM DURATION

(71) Applicant: José António Pacheco Dos Santos Dias, Lisbon (PT)

(72) Inventor: José António Pacheco Dos Santos Dias, Lisbon (PT)

( * ) Notice: Subject to any disclaimer, the term of this patent is extended or adjusted under 35 U.S.C. 154(b) by 958 days.

(21) Appl. No.: 17/418,858

(22) PCT Filed: Dec. 17, 2019

(86) PCT No.: PCT/IB2019/060920
§ 371 (c)(1),
(2) Date: Jun. 28, 2021

(87) PCT Pub. No.: WO2020/136502
PCT Pub. Date: Jul. 2, 2020

(65) Prior Publication Data
US 2022/0071973 A1   Mar. 10, 2022

(30) Foreign Application Priority Data
Dec. 27, 2018   (PT) ........................................ 115231

(51) Int. Cl.
| | | |
|---|---|---|
| *A61K 31/445* | (2006.01) | |
| *A61K 9/00* | (2006.01) | |
| *A61K 9/06* | (2006.01) | |
| *A61K 31/155* | (2006.01) | |
| *A61K 31/167* | (2006.01) | |
| *A61K 47/02* | (2006.01) | |
| *A61K 47/10* | (2017.01) | |
| *A61K 47/14* | (2017.01) | |
| *A61K 47/38* | (2006.01) | |
| *A61P 23/02* | (2006.01) | |

(52) U.S. Cl.
CPC .......... *A61K 31/445* (2013.01); *A61K 9/0034* (2013.01); *A61K 9/06* (2013.01); *A61K 31/155* (2013.01); *A61K 31/167* (2013.01); *A61K 47/02* (2013.01); *A61K 47/10* (2013.01); *A61K 47/14* (2013.01); *A61K 47/38* (2013.01); *A61P 23/02* (2018.01)

(58) Field of Classification Search
CPC .. A61K 31/445; A61K 31/155; A61K 31/167; A61K 9/0034; A61K 9/106; A61K 47/02; A61K 47/10; A61K 47/14; A61K 47/38; A61P 23/02
USPC ........................................................ 514/330
See application file for complete search history.

(56) References Cited

U.S. PATENT DOCUMENTS

2014/0163072 A1   6/2014   Romon-De-Jesus

FOREIGN PATENT DOCUMENTS

| CA | 2925363 A1 | 5/2015 |
|---|---|---|
| WO | 2006096913 A1 | 9/2006 |
| WO | 20180147790 A1 | 8/2018 |

OTHER PUBLICATIONS

Richards et al: "The pharmacology of local anaesthetic drugs", Current Anaesthesia and Critical Care, Churchill Livingstone, London, GB, vol. 6, No. 1, (Jan. 1, 1995), pp. 41-47, XP005210118.
Anonymous: "Summary of Product Characteristics: Instillagel", (Aug. 11, 2014) XP055677061, http://www.pat.nhs.uk/downloads/patient-information-leaflets/urology/Instillagel.pdf.

*Primary Examiner* — Kristin A Vajda
(74) *Attorney, Agent, or Firm* — Rivka Friedman

(57) ABSTRACT

The present invention is enclosed in the medical area, specifically within the area of lubricant gels for transurethral procedures, referring to a gel pharmaceutical composition with an anaesthetic effect of short and long duration, for being administered through the urethra. It is an object of the present invention a gel composition with an anaesthetic effect of short and long term duration for administration through the urethra which comprises a lubricant gel, at least one local short duration anaesthetic composition and at least one local long duration anaesthetic composition which comprises ropivacaine or bupivacaine. The presence of between a long-acting anaesthetic composition in the lubricant gel of the present invention, combined with a short-term acting anaesthetic composition, provides an enormous asset to existing products, because of the immediate and substantially superior and longer-lasting well-being of patients. Advantageously, it is for use as a local anaesthetic with short and long term duration.

16 Claims, No Drawings

GEL COMPOSITION WITH AN ANAESTHETIC EFFECT OF SHORT AND LONG TERM DURATION

FIELD OF THE INVENTION

The present invention is enclosed in the medical area, specifically within the area of lubricant gels for trans-urethral procedures, referring to a gel pharmaceutical composition with an anaesthetic effect of short and long duration, for being administered through the urethra.

PRIOR ART

Numerous situations exist in Medicine where it is necessary to perform procedures through the urethra. More often, it is necessary to place a catheter (i.e. a bladder catheter), which is inserted through the urethra and allows to empty the bladder. For example, before some types of surgery are started, at the end of other surgeries, when the patient is unable to urinate spontaneously and is left with the urine retained inside the bladder (a condition called urinary retention), or when it is necessary to measure the amount of urine that a patient produces in a given time interval.

There are also several trans-urethral procedures (such as diagnostic endoscopies, urethral dilatations, urethral, prostate, bladder, ureter or kidney surgeries) where devices designated as endoscopes (urethroscopes, cystoscopes, resectors, ureteroscopes, among others) or dilators of the urethra, need to be inserted through the urethra.

Before insertion of the catheters, as well as before the endoscopic urological examinations and surgeries (which involve the insertion of devices through the urethra), it is necessary to introduce a lubricant into the urethra (a channel which provides communication between the bladder and the outside), generally in the form of a lubricating gel, so that the placement of said catheter or endoscope is feasible and the least traumatic as possible.

Gel products with a lubricating substance are uniformly used in practice and are routinely used prior to a catheterization or introduction through the urethra of any equipment, accessory or device used for diagnostic or therapeutic purposes. However, the products currently available for this purpose either do not have any anaesthetic effect or have a short-acting anaesthetic effect (short effect meaning several minutes), which means that after a few minutes the presence of the catheter or of the inserted device in the urethra becomes very uncomfortable and often intolerable to patients, disrupting or preventing the performance of such examinations and/or surgeries, and significantly disrupting the quality of life and well-being of patients.

Many patients are kept with such a catheter for long periods of time, ranging from a few hours to several days, lasting up to weeks or months. Pain is most evident in the first few hours, since nerve stimulation is more exuberant within the first few hours after catheter placement.

Often, for example in the post-operative period, and although there are other causes of pain and discomfort (for instance the surgery performed or the incision necessary for its accomplishment), the presence of the catheter is the main factor of disturbance/reduction of the well-being and life quality of the patient.

In fact, pain and/or discomfort due to a catheter is often the most frequent and intense complaint in patients undergoing surgery, and this pain/discomfort is often greater than the pain at the surgical site. In contrast to gels known in the art, the composition of the present invention allows both rapid and prolonged relief of pain and urethral discomfort caused by the presence of catheters or transurethral devices.

The pharmaceutical composition of the present invention is intended to be used immediately prior to the placement of catheters or urethral endoscopes/dilators in a patient, thereby providing the relief of pain and discomfort caused by the presence of these devices in the urethra within the first hours after catheterisation, either in a post-operative or in a context of catheterisation for any other reason.

SUMMARY OF THE INVENTION

It is an object of the present invention a gel composition with an anaesthetic effect of short and long term duration for administration through the urethra which comprises a lubricant gel, at least one local short duration anaesthetic composition and at least one local long duration anaesthetic composition, the local long duration anaesthetic composition comprises ropivacaine and/or bupivacaine, the ratio between the w/w percentage of the local long duration and short anaesthetic compositions being such that the effect of the local long duration anaesthetic composition overlaps with the effect of the local short duration anaesthetic composition. The presence of between a long-acting anaesthetic composition in the lubricant gel of the present invention, combined with a short-term acting anaesthetic composition, provides an enormous asset to existing products, because of the immediate and substantially superior and longer-lasting well-being of patients, the anaesthetic effect being continuous. Advantageously, the local long duration anaesthetic composition specifically comprises ropivacaine hydrochloride, more preferably consisting of ropivacaine hydrochloride or of bupivacaine hydrochloride. Typically, the effect of the local long duration anaesthetic composition starts after the effect of the local short duration anaesthetic composition. Typically, a short term duration is defined as a few minutes (such as 10 minutes from the start of the effect) and a long term duration is defined as a few hours (such as 2 to 10 hours from the start of the effect).

In an inventive aspect of the gel composition of the present invention, the ropivacaine hydrochloride is in a percentage of 0.1% to 5% w/w, preferably 0.75% w/w. In another aspect of the present invention, the local short duration anaesthetic composition comprises lidocaine, preferably comprising lidocaine hydrochloride, and more preferably consisting of lidocaine hydrochloride in an amount of 0.1% to 5% w/w, preferably 2% w/w.

An enhanced combined effect—due to obtaining a suitable intersection between the short-term effect of lidocaine hydrochloride with the longer-term effect of ropivacaine hydrochloride—is provided by an embodiment of the gel composition of the present invention with the combination of ropivacaine hydrochloride as a long-term anaesthetic composition in a percentage of 0.1% to 5% w/w, preferably 0.75% w/w with lidocaine hydrochloride in an amount of 0.1% to 5% w/w, preferably 2% w/w.

Advantageously, the gel composition of the present invention is for use as a local anaesthetic with short-term and long-term duration, preferably for use in treating and/or preventing pain resulting from the introduction through the urethra of a patient of any medical equipment, accessory or device for diagnosis or therapeutic purposes, or for being administered through the urethra before and/or during the introduction through the urethra of a patient of any medical equipment, accessory or device for diagnosis or therapeutic purposes.

DETAILED DESCRIPTION

The more general and advantageous configurations of the present invention are described in the Summary of the invention. Such configurations are detailed below in accordance with other advantageous and/or preferred embodiments of implementation of the present invention.

As referred, the object of the present invention is gel pharmaceutical composition with a short-term and long-term anaesthetic effect, for administration on/through the urethra, the gel being lubricant.

The pharmaceutical composition of the present invention allows to lubricate and anesthetize the urethra, thereby allowing the insertion of different equipment, devices and accessories through that organ (including alloys, endoscopes, urethral dilators, dilator balloons, guide wires, etc.) in a way much more comfortable and tolerable for patients than those known in the art, thus significantly reducing the discomfort and pain associated with these procedures for a longer time.

The combination of a short-acting and long-acting anaesthetic composition allows for rapid and prolonged relief of urethral pain and discomfort.

In an advantageous embodiment of the gel composition of the present invention, it further comprises an anti-septic agent, preferably comprising chlorhexidine, more preferably consisting of chlorhexidine gluconate. Thus, it further contains an antiseptic agent to reduce the risk of infection, which is increased by the prolonged application of the catheter/device/instrument and duration of a procedure.

In a preferred embodiment of the gel composition of the present invention, combinable with any above described, it further comprises one or more excipients, the one or more excipients comprising one or combinations of the following: propylene glycol, hydroxyethylcellulose, methyl para-hydroxybenzoate, propyl para-hydroxybenzoate, sodium hydroxide and purified water.

Advantageously, the gel composition of the present invention has it has a composition of:
 0.1 to 5% of chlorhexidine gluconate,
 0.5 to 10% of lidocaine hydrochloride,
 0.1 to 5% of ropivacaine hydrochloride or 0.05-5% of bupivacaine hydrochloride, and
 a remainder of one or combinations of the following: propylene glycol, hydroxyethylcellulose, methyl para-hydroxybenzoate, propyl para-hydroxybenzoate, sodium hydroxide and purified water.

The referred quantities of chlorhexidine gluconate, lidocaine hydrochloride and ropivacaine hydrochloride provide not only a suitable intersection between the short-term effect of lidocaine hydrochloride with the longer-term effect of ropivacaine hydrochloride but also a suitable intersection between the longer-term anaesthetic effect of ropivacaine hydrochloride and the antiseptic effect of chlorhexidine gluconate.

The composition if preferably of:
 0.1 to 5% of chlorhexidine gluconate,
 0.5 to 10% of lidocaine hydrochloride,
 0.1 to 5% of ropivacaine hydrochloride or 0.05-5% of bupivacaine hydrochloride, and
 a remainder of a combination of the following: propylene glycol, hydroxyethylcellulose, methyl para-hydroxybenzoate, propyl para-hydroxybenzoate, sodium hydroxide and purified water.

The composition of the gel composition of the present invention being more preferably of:
 0.5% of chlorhexidine gluconate,
 2% of lidocaine hydrochloride,
 0.75% of ropivacaine hydrochloride or 0.5% of bupivacaine hydrochloride, and
 a remainder of a combination of the following: propylene glycol, hydroxyethylcellulose, methyl para-hydroxybenzoate (E218), propyl para-hydroxybenzoate (E216), sodium hydroxide and purified water.

Due to the short-term effect of the local short duration anaesthetic composition, and depending on the concentration of such short duration composition, the gel composition of the present invention initiates its anaesthetic effect in 0.5 to 5 minutes.

On the other hand, due to the longer term effect of the local long duration anaesthetic composition, and depending on the concentration of such long duration composition, the gel composition of the present invention continuously maintains its anaesthetic effect until 2 to 10 hours from its start.

With respect to gel compositions comprising lidocaine, the onset of its action is 30 seconds to 5 min and the duration of its action is of 15-20 min. With respect to gel compositions comprising ropivacaine, the onset of its action is of 10-20 min and the duration of action is 2-10 hours. With respect to gel compositions comprising bupivacaine, the onset of its action is of 7-10 min and the duration of action is of up to 7 hours.

Thus, and with regard to the above disclosed w/w compositions, the duration of lidocaine is overlapped with the start of the effect of ropivacaine/bupivacaine, providing an anaesthetic effect which starts in 30 seconds-5 minutes from application of the gel composition and stops within 2-10 hours.

EXAMPLES

A formulation of the pharmaceutical composition of the invention can be obtained by adding to a lubricating gel 2% of lidocaine hydrochloride, 0.75% ropivacaine hydrochloride and 0.5% chlorhexidine gluconate. Such formulation results in a short term anaesthetic effect of 0.5 to 20 minutes (start and stop of the effect) and a long term anaesthetic effect of 5 minutes to 6 hours (start and stop of the effect).

The lubricating gel composition of the present invention is obtained by mixing hydroxyethylcellulose, propylene glycol and purified water. In addition, the pharmaceutical composition may be added methyl para-hydroxybenzoate (E218), propyl para-hydroxybenzoate (E216) and/or sodium hydroxide.

The final product has the following characteristics: viscous, homogeneous, clear, transparent or coloured, odourless.

As will be clear to one skilled in the art, the present invention should not be limited to the embodiments described herein, and a number of changes are possible which remain within the scope of the present invention.

Of course, the preferred embodiments shown above are combinable, in the different possible forms, being herein avoided the repetition all such combinations.

The invention claimed is:

1. A gel composition with an anaesthetic effect of short and long term duration for administration through the urethra characterized in that it comprises a lubricant gel, at least one local short duration anaesthetic composition and at least one local long duration anaesthetic composition, the local long duration anaesthetic composition comprising ropivacaine and/or bupivacaine, the ratio between the w/w percentage of the local long duration and short anaesthetic compositions being such that the effect of the local long duration anaesthetic composition overlaps with the effect of the local short duration anaesthetic composition.

2. A gel composition according to claim 1 wherein the local long duration anaesthetic composition specifically comprises ropivacaine hydrochloride and/or bupivacaine hydrochloride.

3. A gel composition according to claim 2 wherein the local long duration anaesthetic composition specifically consists of ropivacaine hydrochloride.

4. A gel composition according to claim 3 wherein the ropivacaine hydrochloride is in a percentage of 0.1% to 5% w/w.

5. A gel composition according to claim 2 wherein the local long duration anaesthetic composition specifically consists of bupivacaine hydrochloride.

6. A gel composition according to claim 1 wherein the local short duration anaesthetic composition comprises lidocaine.

7. A gel composition according to claim 6 wherein the local short duration anaesthetic composition consists of lidocaine hydrochloride.

8. A gel composition according to claim 7 wherein the lidocaine hydrochloride is in a percentage of 0.1% to 5% w/w.

9. A gel composition according to claim 1 wherein it further comprises an anti-septic agent.

10. A gel composition according to claim 1 wherein it further comprises one or more excipients, the one or more excipients comprising one or combinations of the following: propylene glycol, hydroxyethylcellulose, methyl para-hydroxybenzoate, propyl para-hydroxybenzoate, sodium hydroxide and purified water.

11. A gel composition according to claim 10 wherein it has a composition of:
   0.1 to 5% of chlorhexidine gluconate,
   0.5 to 10% of lidocaine hydrochloride,
   0.1 to 5% of ropivacaine hydrochloride or 0.05-5% of bupivacaine hydrochloride, and
   a remainder of one or combinations of the following: propylene glycol, hydroxyethylcellulose, methyl para-hydroxybenzoate, propyl para-hydroxybenzoate, sodium hydroxide and purified water.

12. A gel composition according to claim 11 wherein it has a composition of:
   0.1 to 5% of chlorhexidine gluconate,
   0.5 to 10% of lidocaine hydrochloride,
   0.1 to 5% of ropivacaine hydrochloride or 0.05-5% of bupivacaine hydrochloride, and
   a remainder of a combination of the following: propylene glycol, hydroxyethylcellulose, methyl para-hydroxybenzoate, propyl para-hydroxybenzoate, sodium hydroxide and purified water.

13. A gel composition according to claim 12 wherein it has a composition of:
   0.5% of chlorhexidine gluconate,
   2% of lidocaine hydrochloride,
   0.75% of ropivacaine hydrochloride or 0.5% of bupivacaine hydrochloride, and
   a remainder of a combination of the following: propylene glycol, hydroxyethylcellulose, methyl para-hydroxybenzoate, propyl para-hydroxybenzoate, sodium hydroxide and purified water.

14. A gel composition according to claim 1 for use as a local anaesthetic with short-term and long-term duration.

15. A gel composition according to claim 14 for use in treating and/or preventing pain resulting from the introduction through the urethra of a patient of any medical equipment, accessory or device for diagnosis or therapeutic purposes.

16. A gel composition according to claim 15 for being administered through the urethra before and/or during the introduction through the urethra of a patient of any medical equipment, accessory or device for diagnosis or therapeutic purposes.

* * * * *